United States Patent [19]

Wardlaw et al.

[11] 4,181,609

[45] Jan. 1, 1980

[54] BLOOD CONSTITUENTS TESTING METHOD

[76] Inventors: Stephen C. Wardlaw, 128 Sunset Hill Dr., Branford, Conn. 06405; James V. Massey, III, 80 Driftwood La., Trumbull, Conn. 06610; Robert A. Levine, 31 Pilgrim La., Guilford, Conn. 06437

[21] Appl. No.: 959,462

[22] Filed: Nov. 13, 1978

Related U.S. Application Data

[60] Continuation-in-part of Ser. No. 862,543, Dec. 20, 1977, Pat. No. 4,137,755, which is a division of Ser. No. 724,563, Sep. 20, 1976, Pat. No. 4,082,085, which is a division of Ser. No. 673,058, Apr. 2, 1976, Pat. No. 4,027,660.

[51] Int. Cl.² .............................................. B01D 17/00
[52] U.S. Cl. ...................................... 210/72; 210/83; 210/DIG. 23
[58] Field of Search ..................... 422/44, 46; 210/71, 210/72, 73R, 83, 78, 83, DIG. 23, DIG. 24; 73/53; 128/214 A, DIG. 5, DIG. 22; 233/1 R, 26

[56] References Cited

U.S. PATENT DOCUMENTS

| 2,876,769 | 3/1959 | Cordova | 128/214 A |
|---|---|---|---|
| 3,443,060 | 5/1969 | Smith | 128/214 A |

*Primary Examiner*—Frank Sever
*Attorney, Agent, or Firm*—William W. Jones

[57] ABSTRACT

A method whereby separation of red cells from white cells in a centrifuged blood sample is improved. An effective amount of potassium oxalate is added to the blood sample to increase the density of the red cells. The blood sample is then warmed to minimize the increase in density of the white cells which otherwise occurs in certain cases.

2 Claims, No Drawings

BLOOD CONSTITUENTS TESTING METHOD

This application is a continuation-in-part of application Ser. No. 862,543, filed Dec. 20, 1977, now U.S. Pat. No. 4,137,755, issued Feb. 6, 1979, which in turn is a division of application Ser. No. 724,563, filed Sept. 20, 1976, now U.S. Pat. No. 4,082,085, which in turn is a division of application Ser. No. 673,058, filed Apr. 2, 1976, now U.S. Pat. No. 4,027,660.

This invention is related to the invention disclosed and claimed in application Ser. No. 910,807, filed May 30, 1978, and relates generally to improvements in a method for measuring blood constituent volumes.

We have invented a method and apparatus with which preliminary measurements of the white cell, platelet, and differential white cell counts in anticoagulated whole blood can be made. The method involves the use of a capillary tube which contains an elongated insert body which floats on, or slightly in, the red cell layer in a centrifuged sample of anticoagulated whole blood. The insert body combines with the bore wall of the capillary tube to form an annular free space which is occupied by the buffy coat of the centrifuged blood sample. Due to its being forced to settle into a very restricted space, the axial boundaries of the buffy coat and its constituent cell layers are spaced further apart than normal whereby the height of each cell layer can be visually measured while the sample remains in the capillary tube. An instrument with which such measurements can be made is disclosed in application Ser. No. 788,509, filed Apr. 8, 1977. A stain such as acridine orange is added to the blood sample to differentially color the various cell types, thereby rendering the cell band interfaces readily visible.

A compound which selectively densifies certain of the cell types, namely the red cells, is also preferably added to the sample in order to render the interface between the red cell layer and the white cell layer more sharply defined. This improved cell band interface delineation is accomplished by increasing the density of the red cells without significantly increasing the density of the white cells. This causes any immature red cells which may be present in the sample to settle down into the red cell layer instead of floating up into and co-mingling with the lighter white cells. This latter phenomenon has been observed in certain untreated blood samples and results in an undesirably hazy red cell-white cell interface being formed. Potassium oxalate is the densifying compound which is preferred for use. The concentration of potassium oxalate needed to produce the required degree of red cell densification is in the range of about 400 mg/dl to about 600 mg/dl in solution.

The stain and potassium oxalate are preferably dry coated onto the tube bore wall and placed into solution by the blood sample as it is drawn into the tube.

We have discovered that even with the addition of the potassium oxalate solution to the blood sample, there still will occur, in about 5-10% of the samples tested, poor separation between the red cells and white cells with a resultant poorly defined interface. Most notably, this poor separation is observed with some patients who are confined to hospitals for extended time periods, or who are seriously ill. The exact cause of poor cell separation in this population of patients is not completely understood.

We have found that this failure to achieve timely proper separation of the red cells from the white cells can be corrected by heating the blood sample prior to centrifugation of the blood sample. The sample is drawn into the capillary tube, mixed, heated for an appropriate length of time and then centrifuged. Good separation is then noted, whereupon a reading can be taken.

The temperatures to which the sample is to be heated to obtain effective separation have been found to be in the range of about 41°–45° C. The sample should be kept in the heated temperature range for an incubation period of 3–10 minutes. We prefer to heat the blood sample to a temperature of about 43° C. for a period of about 5 minutes whereupon vastly improved cell separation is observed in most cases.

The heating step can be accomplished by placing a rack of sealed tubes in a heated water bath, or by utilizing a heated rack per se having a series of recessed slots, or the like, into which the tubes will nest.

The following is a specific example whereby the invention may be carried out. The bore of a capillary tube of the type conventionally used for measuring blood samples is wet-coated with an acridine orange stain and a solution containing about 0.7 mg of potassium oxalate, dissolved in water. The water is evaporated from the tube bore leaving a dry coating of the stain and the potassium oxalate on the wall of the tube bore. A generally cylindrical insert body of proper dimensions is inserted into the tube bore and may be held in place with a small amount of a water-soluble adhesive, such as sugar. A blood sample of approximately 110 microliters is drawn into and fills the capillary tube. The capillary tube is then agitated by hand to mix the stain, the potassium oxalate, and the blood together, the reagents being soluble in blood. The tube is then heated to warm the blood-reagent mixture to a temperature of about 43° C., which temperature is maintained for a period of about five minutes. The sample is then centrifuged in a conventional blood centrifuge for about five minutes to separate out the respective blood layers and position the insert on top of the red cell layer. The separation of red cells from white cells which is observed is excellent, and the interface between the red and white cells is sharply defined. Comparison with samples of the same blood taken from hospitalized or seriously ill persons which were treated exactly as described above, with the exception that the heating step was omitted, shows far superior separation in the heated samples as compared to the non-heated samples.

Since many changes and variations of the disclosed embodiment of the invention may be made without departing from the inventive concept, it is not intended to limit the invention otherwise than as required by the appended claims.

What is claimed is:

1. In a method for obtaining a clearly defined interface between the red cell layer and the white cell layer in a sample of anticoagulated blood which comprises the steps of adding a red cell densifying compound to said sample and subsequently centrifuging said sample, the improvement comprising the step of heating the blood sample prior to centrifugation thereof to a temperature in the range of about 41° C. to about 45° C. for an incubation period in the range of about three minutes to about ten minutes prior to said centrifuging step.

2. The method of claim 1, wherein said sample is heated to a temperature of 43° C. for an incubation period of five minutes.

* * * * *